United States Patent [19]

Mangold et al.

[11] Patent Number: 5,106,752
[45] Date of Patent: Apr. 21, 1992

[54] METHOD AND REAGENT FOR DETERMINING THE IONIC STRENGTH OR SPECIFIC GRAVITY OF AQUEOUS LIQUIDS

[75] Inventors: Dieter Mangold, Maxdorf; Brigitte Gambke, Mannheim, both of Fed. Rep. of Germany

[73] Assignee: Boehringer Mannheim GmbH, Mannheim, Fed. Rep. of Germany

[21] Appl. No.: 615,372

[22] Filed: Nov. 19, 1990

Related U.S. Application Data

[62] Division of Ser. No. 371,208, Jun. 26, 1989, Pat. No. 5,064,615.

[30] Foreign Application Priority Data

Jul. 8, 1988 [DE] Fed. Rep. of Germany ....... 3823151

[51] Int. Cl.$^5$ ................... G01N 9/00; G01N 21/75
[52] U.S. Cl. ............................... 436/2; 436/74; 436/163; 436/169

[58] Field of Search .............. 436/2, 74, 79, 163, 436/169

[56] References Cited

U.S. PATENT DOCUMENTS 4,670,218 6/1987 Gantzer ........................... 422/56

FOREIGN PATENT DOCUMENTS 0023611 2/1983 European Pat. Off. .

Primary Examiner—Robert J. Hill, Jr.
Assistant Examiner—David Redding
Attorney, Agent, or Firm—Felfe & Lynch

[57] ABSTRACT

The ionic strength or the specific gravity of an aqueous liquid is determined by mixing the liquid with a reagent composition which contains at least one pH buffer substance but no polyelectrolyte polymer, or at least one pH buffer substance and/or at least one complex former, determining the pH of the mixture, and evaluating the determined value.

28 Claims, No Drawings

METHOD AND REAGENT FOR DETERMINING THE IONIC STRENGTH OR SPECIFIC GRAVITY OF AQUEOUS LIQUIDS

This application is a divisional of Ser. No. 371,208, filed June 26, 1989, now U.S. Pat. No. 5,064,615.

FIELD OF THE INVENTION

This invention relates to a novel method for determining the ionic strength or the specific gravity of aqueous liquids, and to a reagent composition for use in the performance of said method.

BACKGROUND OF THE INVENTION AND THE PRIOR ART

Several physical methods are known for the determination of the specific gravity of urine, for example the determination with hydrometers, urinometers, pyknometers and refractometers. These methods are admittedly of sufficient exactitude but require a high instrument expense and are time-consuming and costly due to the necessary cleaning and calibration of the apparatus.

The measurement of the specific gravity with the aid of so-called test strips, which can also be evaluated visually, is simpler. The test strips have a test area which contains appropriate reagents. The determination can take place in a simple way by dipping the test strip into a urine sample and observing the coloration of the test area. Furthermore, the test strips offer the advantage of being combinable with other urine tests, for example for the detection of glucose, leukocytes, blood and the like, in a multiple test strip with a corresponding number of test areas spaced from one another. The measurement of the specific gravity of urine can then take place, with a saving of time, in one step, in addition to the measurement of these other parameters. The evaluation can also be carried out with the use of appropriate apparatus.

A method for determining the specific gravity of urine with a test strip is described in U.S. Pat. No. 4,015,462. A carrier matrix is provided with osmotically breakable microcapsules which contain a liquid; when such a matrix is brought into contact with a sample solution of lower osmolality, the hydrostatic pressure increases in the microcapsules, the walls of which consist of semi-permeable membrane material. This leads to a rupture of the microcapsules. The rupture of the microcapsules and the resulting release of a dye dissolved in the liquid leads to a coloration of the matrix. The intensity of the coloration is proportional to the osmolality or to the specific gravity of the sample solution. A disadvantage of this method is the use of a carrier matrix provided with microcapsules since the production thereof is very difficult because of the necessary exactitude.

A further method for determining the specific gravity or the ionic strength with a test strip is described in U.S. Pat. No. 4,318,709 and the corresponding Federal Republic of Germany Patent Specification No. 29 44 980. In this method the sample is mixed with a reagent which contains a weakly acidic or weakly basic polyelectrolyte polymer neutralized to an extent of at least 50% and an indicator. The fundamental principle is the proportionality between the specific gravity and the ionic strength of an aqueous solution.

Polyelectrolyte polymers are there designated as being polymers with ionic groups, polyacrylic acid and polyvinylamine being mentioned by way of example.

European Patent Specification No. 0,114,315 describes a reagent which contains a weakly basic polyelectrolyte polymer neutralized by a strong organic acid and an indicator.

European Patent Specification No. 0,114,316 discloses a reagent which contains a weakly acidic polyelectrolyte polymer, in which at least one carboxyl group is present in the form of an ammonium salt, and an indicator.

European Patent Specification No. 0,023,631 discloses a reagent for determining the ionic strength or the specific gravity. Besides a strongly acidic or strongly basic polyelectrolyte polymer, it contains a buffer substance which ensures a pH value of at least 6.5, as well as a pH indicator.

However, methods which make use of a reagent which contains a polyelectrolyte polymer have the disadvantage that the color brought about by the pH shift changes in the course of time. The result of this color change is that the reading for the specific gravity after 1 minute differs very greatly from the reading after 2 or even 5 minutes.

Thus, if the test is carried out by persons who are not specifically trained for the purpose, such as patients, and the evaluation is not always undertaken at the same time as indicated by the producer of the strip, the readings can lead to seriously erroneous interpretations of the state of the health of a patient.

Therefore, there is a need for a method for determining the ionic strength or the specific gravity of aqueous liquids which provides test results which remain constant during the test over a comparatively long period of time.

OBJECTS OF THE INVENTION

It is an object of the present invention to satisfy this need and to provide methods which can be carried out rapidly and dependably on a test carrier.

DESCRIPTION OF THE INVENTION

Thus, the present invention provides a method for determining the ionic strength or the specific gravity of an aqueous liquid, which comprises mixing the liquid with an appropriate reagent, determining the pH value in the liquid and evaluating the reading, where the reagent contains at least one pH buffer substance but no polyelectrolyte polymer or at least one pH buffer substance and/or at least one complex former.

The present invention also provides a reagent for determining the ionic strength or the specific gravity of an aqueous liquid, which contains at least one pH buffer substance but no polyelectrolyte polymer or at least one pH buffer substance and/or at least one complex former.

The aqueous liquid the ionic strength of which, also called osmolality, or the specific gravity of which can be determined by the method according to the present invention consists essentially of water. Further components of the liquid can be dissolved and/or undissolved components. Dissolved components are ionic and nonionic substances. Undissolved components can be sparingly soluble chemical substances but also other materials, such as biological substances, for example cells.

The liquid can have any desired pH value. However, the method is preferably used to investigate liquids with a pH value of 3 to 13 and especially those with a pH of 4 to 9. Liquids with another pH value can also be investigated if the pH value thereof is brought into this range by the addition of an acid or base before or during the determination.

If the method is used for the determination of the specific gravity, it can be used for a range of values of the specific gravity of 0.95 to 2, and preferably of 0.99 to 1.2.

Preferred aqueous liquids are salt solutions and body fluids. The method of the present invention is especially well suited for body fluids, such as perspiration or urine. In particular, it has proved to be useful for urine investigations. For this purpose, a sample of the urine can be admixed with the reagent without further preparative steps, since not only the specific gravity of the urine with values of 1.00 to 1.04 but also the pH value of the urine with values of 4.5 to 8.0 normally lie in the range preferred for the method according to the present invention.

The reagent with which the liquid is admixed contains at least one pH buffer substance and/or at least one complex former. pH buffers are well known substances. A pH buffer substance is a mixture of a weak acid with a practically completely dissociated salt of this acid or a mixture of a weak base with a practically completely dissociated salt of this base. This is described, for example, in *Rompps Chemie Lexikon*, 8th edition, Volume 5, key word "Puffer", which also describes the action of solutions of these buffer substances towards added acids and bases; the pH value of the buffer scarcely changes when acids or bases are added thereto.

According to the present invention, for the determination of the ionic strength or of the specific gravity especially of urine, pH buffer substances the pK value of which in water is from 4 to 12 and preferably from 5.5 to 10 can be used as a reagent. Of these, buffer substances with the smallest possible activity coefficient are preferred. The activity coefficient is especially small in the case of buffer substances which are made up from ions with a high effective charge. The activity coefficients of ions and buffer substances in aqueous solutions are known or can be simply determined in known manner (see F. Seel, *Grundlagen der analytischen Chemie*, published by Verlag Chemie, Weinheim, Federal Republic of Germany; and the brochure "Buffers" of the firm Calbiochem, 1985, pages 12-15). Buffer substances, the activity coefficient of which at a concentration of 0.1 M is less than 1 and preferably less than 0.9 have proved to be especially preferred.

Such buffer substances are, in a pH range of 4 to 11, for example buffers which contain the following ions: phosphate, borate, carbonate, citrate, diethylmalonate or nitrilo-tris-methylenephosphonate. Zwitterionic buffers, for example glycine buffer or 2-(N-morpholino)-ethanesulphonic acid (MES) can also be used.

Complex formers within the scope of the present invention are chemical substances which react with ions resulting in complex formation. Especially preferred are complex formers which release at least one proton upon complex formation with ions.

Such complex formers include, for example, crown ethers, cryptands, podands and multi-dentate ligands which contain weakly acidic or weakly basic groups, for example carboxyl or amino groups. Preferred complex formers are those which can complex a maximum of one ion per molecule. For the especially exact detection of the ionic strength or of the specific gravity the complex former must be able to form complexes with, if possible, all ions present in the liquid, especially the cations, such as alkali metal and alkaline earth metal ions, which occur frequently, for example, in urine. Therefore, the following compounds can, for example, be used as complex formers:

crown ethers, cryptands, podands: 18-crown-6-tetracarboxylic acid, N-phenylaza-15-crown-5, hexacylene trisulfate, Kryptofix 222 ®, Kryptofix221 ® and Kryptofix 211 ®, multi-dentate ligands: ethylenediamine-tetraacetic acid, nitrilotriacetic acid, diethylenetriamine=pentaacetic acid, di-(2-aminoethoxy)-ethane-tetraacetic acid, hexamethylenedinitrilotetraacetic acid, nitrilodiacetic acid and N-methylaminodiacetic acid.

For determination of the ionic strength or of the specific gravity of liquids which mainly contain dissolved salts which display no substantial buffer capacity, the method of the instant invention most preferably performed with a reagent which consists mainly of one or more complex formers. In this case, the reagent must not necessarily contain pH buffer substances.

If the specific gravity of a liquid is to be determined which comprises substances with appreciable buffer capacity, for example weak bases or acids or salts thereof, a reagent is preferred which contains at least one pH buffer substance. In that case, the contribution of non-ionic compounds, which also be contained in the liquid, to the specific gravity is also taken into account. In addition, the reagent can then also contain one or more complex formers. For the investigation of urine, a reagent composition should be chosen which, dissolved in an amount of water equivalent to the sample, has a pH value of preferably greater than 5.5.

For reasons of simplicity, it is expedient to keep the number of components of the reagent composition as small as possible. Therefore, it is also very advantageous to select as a buffer substance one which, over and above its pH-buffering action, also has anion-complexing action. Such substances include, for example, nitrilo-tris-(methylenephosphonic acid) and pentasodium triphosphate ($Na_5P_3O_{10}$).

The composition of the reagent, especially with regard to its pH value, is preferably so chosen that the pH value after dissolving the reagent in an amount of water equal to the sample is approximately the same as or, especially preferably, greater than the pH value of the liquid to be investigated. The most appropriate pH value can readily be determined by means of a few experiments.

In the case of a reagent applied to an absorbent carrier, this is very easy to accomplish. The pH value of the impregnation solution is then appropriately adjusted before the impregnation, for example in the case of a reagent for the determination of the specific gravity of urine to a pH value of 6 to 11 and preferably of 7 to 9.

The amount of pH buffer substances and/or complex formers in the reagent, referred to the amount of liquid to be investigated and mixed therewith, is so chosen that the end concentration of these composition reagent components in the sample liquid totals 0.005 to 1.0 mol/liter and preferably 0.005 to 0.2 mol/liter. The form in which the reagent composition is present is not of substantial importance for the determination. For example, the reagent can be used as a powder or tablet, or in the form of a solution.

In the case of the preferred embodiment of the method on a test strip, the reagent is advantageously applied as a coating to an absorbent carrier, preferred carriers being porous carrier materials or fleeces, fleeces being understood to be paper-like carriers made of fibers. Absorbent carriers impregnated with reagent are preferably produced by impregnating the absorbent carrier material with a solution of the reagent and drying it, whereby a reagent film is formed on the whole surface and preferably also on the inner surface.

The reagent can also be applied with film-forming and swellable additive materials to a carrier, for example directly on to the test strip. Furthermore, the reagent can contain conventional additive materials, for example stabilizers, wetting agent and/or swelling agents.

The mixing of the test liquid with the reagent takes place in a manner which is advantageous for the form chosen for the reagent. If the reagent is applied as a coating to an absorbent carrier, the carrier can simply be brought into contact with the liquid. The test liquid is then distributed in the carrier and dissolves off the reagents. This dissolving procedure proceeds especially quickly and completely with the reagent of the method according to the present invention since the reagents are readily soluble lower molecular weight substances.

Due to the action of the reagent on the test liquid, its pH adjusts to a value which is dependent upon the ionic strength or the specific gravity of the test liquid.

This pH value is determined in the method according to the present invention. This determination can take place in known manner, for example also with a pH electrode. The determination with the aid of a pH indicator is especially advantageous since it can then also be carried out visually and without additional apparatus.

It is a prerequisite that a pH indicator be used which displays a color change in a pH range that includes the pH which adjusts in the test liquid. Such pH indicators and color change ranges thereof are known. For the determination of the ionic strength or of the specific gravity of urine, pH indicators with a pK value of 4 to 12 can be used. Of these, bromothymol blue and thymol blue have proved to be especially suitable.

The pH indicator can be added to the reagent or to the liquid to be investigated even before the mixing, or it can be added after the mixing or during the mixing of the reagent with the test liquid. The amount of added indicator is such that the color change can be clearly discerned. Preferred concentrations of the indicator in the mixture of reagent and test liquid sample are from 0.1 to 100 mmol/liter and more preferably from 1 to 50 mmol/liter.

While it is possible to carry out the reaction of the reagent with the aqueous test liquid in a two-phase system, for example in two liquid phases which are not or only slightly miscible with one another, at least a part of the reagent being present in the non-aqueous phase, it is preferable if, during the reaction of the reagent with the test liquid or its components, all the reagents and especially the pH buffer substances or complex formers and possibly also the pH indicator are dissolved in one phase and preferably in the aqueous phase. In this case, the reaction proceeds especially quickly.

The evaluation in the method according to the present invention can take place in an especially simple way. For example, by means of a calibration curve, the determined pH value can be associated with the related ionic strength or the specific gravity. The calibration curve is obtained by determining the pH values for comparable solutions which have, in each case, different but known ionic strengths or different but known specific gravities. In the case of a visual pH determination with the aid of a pH indicator, the resultant color can, for example, also be compared with colors which have been obtained and recorded for a series of liquids of known ionic strength or specific gravity, for example in a color scale.

The evaluation can even be undertaken less than one minute after mixing the reagent and aqueous test liquid sample. The method according to the present invention has the advantage that the determined pH value is still constant even more than 5 minutes after mixing. This is especially important when the evaluation requires a comparatively long time or the evaluation is to be repeated a short time after the first evaluation for reasons of certainty.

An especially preferred embodiment of the method according to the present invention is one for the determination of the specific gravity of urine on a test strip. The test strip has a test area which consists of a fleece which has been impregnated with a solution of the reagent and then dried. The reagent can be a mixture of a pH buffer substance, for example a phosphate buffer which, when dissolved in water, displays a pH value of 8; a complex former, for example nitrilotriacetic acid; and a pH indicator, for example bromothymol blue. The test area is brought into contact with the urine sample to be investigated, for example by dipping the test strip into the urine sample and taking it out as soon as the test area is wet. The color which the test area has then assumed is compared with the color of a standard accompanying the test strip, where each color of the standard is associated with a specific gravity. The specific gravity to be determined has the value which is associated with the standard with coinciding color.

The following examples illustrate the present invention and will enable others skilled in the art to understand it more completely. It should be understood, however, that the invention is not limited solely to the particular examples given below.

EXAMPLE 1

Production of a test strip for the determination of the ionic strength of of the specific gravity of salt solutions or urine a) A cellulose fleece (type 23 SL of the firm Schleicher & Schüll) was impregnated with an aqueous solution of the following composition:
Nitrilo-tris-(methylenephosphonic acid): 120 mM
Bromothymol blue: 0.15% by wt.

The pH value of the solution was adjusted to 8 with a 3.5 N aqueous tetramethylammonium hydroxide solution.

The fleece was dried and cut into a piece the size of $5 \times 5$ mm, and the so produced test area was stuck on to a plastic strip ($100 \times 5$ mm).

b) A cellulose fleece (type 23 SL of the firm Schleicher & Schüll) was impregnated with an aqueous solution of the following composition:
Pentasodium triphosphate ($Na_5P_3O_{10}$): 60 mM
Bromothymol blue: 0.15% by wt.

The pH value of the solution was adjusted to 8 with 2 N hydrochloric acid.

The fleece was dried and cut into a piece the size of $5 \times 5$ mm, and the so produced test area was stuck on to a plastic strip ($100 \times 5$ mm).

c) A cellulose fleece (type 2316 of the firm Binzer) was impregnted with an aqueous solution of the following composition:
Ethylenediamine-tetraacetic acid: 0.2% by wt.
Sodium tetraborate: 60 mM
Thymol blue: 0.1% by wt.

The pH value of the solution was adjusted to 10 with a 10 N aqueous sodium hydroxide solution.

The fleece was dried and cut into a piece the size of a 5×5 mm, and the so produced test area was stuck on to a plastic strip (100×5 mm).

d) A cellulose fleece (type 23 SL of the firm Schleicher & Shüll) was impregnated with an aqueous solution of the following composition:
Sodium dihydrogen phosphate: 60 mM
2-(N-morpholino)-ethanesulphonic acid (MES): 40 mM
Bis-(aminoethyl)-glycol ether N,N,N',N'-tetraacetic acid: 0.75% by wt.
Bromothymol blue: 0.15% by wt.

The pH value of the solution was adjusted to 8 with a 10 N aqueous sodium hydroxide solution.

The fleece was dried and cut into a piece the size of 5×5 mm, and the so produced test area was stuck on the a plastic strip (100×5 mm).

e) A cellulose fleece (type 2316 of the firm Binzer) was impregnated with an aqueous solution of the following composition:
Sodium dihydrogen phosphate: 30 mM
Nitrilotriacetic acid: 0.2% by wt.
Bromothymol blue: 0.1% by wt.

The pH value of the solution was adjusted to 8 with a 10 N aqueous sodium hydroxide solution.

The fleece was dried and cut into a piece the size of 5×5, and the so produced test area was stuck on to a plastic strip (100×5 mm).

f) A cellulose fleece (type 23 SL of the firm Schleicher & Schüll) was impregnated with an aqueous solution of the following composition:
Ethylenediamine-tetraacetic acid: 0.2% by wt.
Sodium dihydrogen phosphate: 30 mM
Bromothyl blue: 0.1% by wt.

The pH value of the solution was adjusted to 8 with a 10 N aqueous sodium hydroxide solution.

The fleece was dried and cut into a piece the size of 5×5 mm, and the so produced test area was stuck on to a plastic strip (100×5 mm).

g) A cellulose fleece (type 23 SL of the firm of Schleicher & Schüll) was impregnated with an aqueous solution of the following composition:
Diethylmalonic acid: 50 mM
Nitrilotriacetic acid: 0.5% by wt.
Bromothymol blue: 0.15% by wt.

The pH value of the solution was adjusted to 8 with a 3.5 N tetramethylammonium hydroxide solution.

The fleece was dried and cut into a piece the size of 5×5 mm, and to produced test area was stuck on to a plastic strip (110×5 mm).

EXAMPLE 2

Determination of the specific gravity of a urine sample

A test strip produced according to Example 1 was briefly dipped into a urine sample. After 30 seconds, 1 minute, 2 minutes and 5 minutes, respectively, the color of the test area was compared with the color of a color scale which had been obtained for urine samples of known specific gravity. The values obtained for the specific gravity at the above-given measurement times were the same. The specific gravity values agreed with the specific gravity value of the same urine specimen determined by means of a pyknometer.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. Method for determining ionic strength or specific gravity of an aqueous liquid, comprising:

contacting said liquid with a non-polyelectrolyte polymer containing reagent comprising (i) a pH buffer substance and (ii) a pH indicator to form an aqueous solution of said aqueous liquid and reagent; and measuring pH of said solution after said contacting as a measure of ionic strength or specific gravity of said aqueous liquid.

2. Method of claim 1, wherein said buffer has an activity coefficient of less than 1 at a concentration of 0.1 M.

3. Method of claim 2, wherein said buffer contains at least one ion selected from the group consisting of phosphate, borate, carbonate, citrate, diethylmalonate and nitrilo-tris-methylene phosphonate.

4. Method of claim 1, wherein said buffer has a pK value of from 4 to 12.

5. Method of claim 4, wherein said buffer has a pK value of from 5.5 to 10.

6. Method of claim 1, wherein said buffer is zwitterionic.

7. Method of claim 6, wherein said buffer contains glycine or 2-(N-morpholino)-ethane sulphonic acid.

8. Method of claim 1, wherein said buffer has ion-complexing ability.

9. Method of claim 8, wherein said ion complexing substance is nitrilo-tris-(methylene-phosphonic) acid or pentasodium triphosphate.

10. Method of claim 1, wherein said reagent is in the form of a solution.

11. Method for determining ionic strength or specific gravity of an aqueous liquid comprising:

contacting said liquid with a reagent consisting essentially of (i) a cation complex former which releases a proton upon complexation of a cation therewith and (ii) a pH indicator to form an aqueous solution of said aqueous liquid and said reagent, under conditions favoring complexing of cations in said aqueous liquid to said complex former with release of protons therefrom, and measuring the pH of said solution as a measure of ionic strength or specific gravity of said aqueous liquid.

12. Method of claim 11, wherein said reagent is impregnated on an absorbent carrier.

13. Method of claim 11, wherein said liquid is urine.

14. Method of claim 11, wherein said complex former is a crown ether, a cryptand, a podand or a multi-dentate ligand.

15. Method of claim 11, wherein said reagent is used at a concentration of from 0.005 to 1.0 mole/liter of liquid.

16. Method of claim 15, wherein said reagent is used at a concentration of from 0.005 to 0.2 mole/liter of liquid.

17. Method of claim 11, wherein said reagent is a powder, tablet or solution.

18. Method of claim 3, wherein said pH indicator displays a color change when said complex former complexes to said cations.

19. Method of claim 11, wherein said pH indicator is bromothymol blue or thymol blue.

20. Method of claim 11, wherein said pH indicator is added at a concentration of from 0.1 to 100 mmol/liter.

21. Method of claim 20, wherein said pH indicator is added at a concentration of from 1 to 50 mmol/liter.

22. Method of claim 11, comprising measuring the pH at a time interval of less than one minute after adding said reagent.

23. Method of claim 11, wherein said reagent is in the form of a solution.

24. Method of claim 11, wherein said reagent does not contain a polyelectrolyte polymer.

25. Method for determining ionic strength or specific gravity of an aqueous liquid which contains a pH buffer substance, comprising:

contacting said aqueous liquid with a solution containing a reagent consisting essentially of (i) a pH buffer substance and (ii) a cation complex former which releases at least one proton upon complexation of a cation therewith to form an aqueous solution of said aqueous liquid and reagent and measuring pH of said solution as a measure of ionic strength or specific gravity of said aqueous liquid.

26. Method of claim 25, wherein said reagent does not contain a polyelectrolyte polymer.

27. Method of claim 17 wherein said cation complex former is bis-(aminoethyl)-glycolether N,N,N',N'-tetraacetic acid.

28. Method of claim 25, wherein said cation complex former is bis-(aminoethyl)-glycolether N,N,N',N'-tetraacetic acid.

* * * * *

UNITED STATES PATENT AND TRADEMARK OFFICE
CERTIFICATE OF CORRECTION

PATENT NO. : 5,106,752
DATED : April 21, 1992
INVENTOR(S) : Dieter Mangold, et. al.

It is certified that error appears in the above-indentified patent and that said Letters Patent is hereby corrected as shown below:

Column 9, Claim 18, line 1, change "claim 3" to -- claim 11 --.

Column 10, Claim 27, line 1, change "claim 17" to -- claim 11 --.

Signed and Sealed this

Nineteenth Day of October, 1993

Attest:

BRUCE LEHMAN

*Attesting Officer*     *Commissioner of Patents and Trademarks*